United States Patent
Evans et al.

(10) Patent No.: US 8,777,968 B2
(45) Date of Patent: *Jul. 15, 2014

(54) SYSTEM, APPARATUS AND METHOD FOR FASTENING TISSUE

(75) Inventors: David J. Evans, Irvine, CA (US); Thomas R. Findlay, III, Ladera Ranch, CA (US); David Zarbatany, Laguna Niguel, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/595,790

(22) Filed: Aug. 27, 2012

(65) Prior Publication Data

US 2013/0053870 A1 Feb. 28, 2013

Related U.S. Application Data

(63) Continuation of application No. 11/174,357, filed on Jun. 30, 2005, now Pat. No. 8,252,005.

(51) Int. Cl.
*A61B 17/04* (2006.01)

(52) U.S. Cl.
USPC ............ 606/144; 606/139; 606/148; 606/170

(58) Field of Classification Search
USPC ......... 606/139–148, 232, 213, 151, 108, 167, 606/180, 172, 170
See application file for complete search history.

(56) References Cited

U.S. PATENT DOCUMENTS

| | | | | |
|---|---|---|---|---|
| 5,334,199 | A * | 8/1994 | Yoon .............................. | 606/144 |
| 5,454,820 | A * | 10/1995 | Kammerer et al. ........... | 606/148 |
| 5,766,217 | A * | 6/1998 | Christy ......................... | 606/148 |
| 5,797,928 | A * | 8/1998 | Kogasaka ...................... | 606/144 |
| 6,165,183 | A * | 12/2000 | Kuehn et al. .................. | 606/139 |
| 6,610,072 | B1* | 8/2003 | Christy et al. ................. | 606/148 |
| 7,628,797 | B2* | 12/2009 | Tieu et al. ..................... | 606/148 |
| 8,226,666 | B2* | 7/2012 | Zarbatany et al. ............ | 606/139 |
| 2003/0144673 | A1* | 7/2003 | Onuki et al. ................... | 606/139 |
| 2003/0181926 | A1* | 9/2003 | Dana et al. ..................... | 606/148 |
| 2004/0111095 | A1* | 6/2004 | Gordon et al. ................. | 606/108 |
| 2004/0153074 | A1* | 8/2004 | Bojarski et al. ................. | 606/72 |
| 2004/0162569 | A1* | 8/2004 | Sikora et al. .................. | 606/148 |
| 2004/0181238 | A1* | 9/2004 | Zarbatany et al. ............ | 606/108 |
| 2006/0047314 | A1* | 3/2006 | Green .......................... | 606/232 |
| 2007/0106309 | A1* | 5/2007 | Onuki et al. .................. | 606/139 |
| 2007/0173865 | A1* | 7/2007 | Oren et al. .................... | 606/148 |

* cited by examiner

*Primary Examiner* — Mark Mashack
(74) *Attorney, Agent, or Firm* — Richard B. Cates (57) ABSTRACT

A tissue fastening device includes a suture clip holder and a suture cutter. A suture clip can be releasably secured to the suture clip holder, and a suture line or lines can pass through the clip and adjacent the suture cutter. A first movement of a control handle causes the suture clip to be released from the suture clip holder, and a second movement of the control handle causes the suture cutter to cut the suture line or lines. The first movement is different from the second movement. The first movement can be rotational, with the second movement being longitudinal. Alternatively, the first movement can be longitudinal, with the second movement being rotational. The device may include a main body, an inner body, and an outer body.

5 Claims, 12 Drawing Sheets

SYSTEM, APPARATUS AND METHOD FOR FASTENING TISSUE

CROSS REFERENCE TO RELATED APPLICATIONS

This application is a continuation of U.S. patent application Ser. No. 11/174,357, filed Jun. 30, 2005, entitled "System, Apparatus, and Method for Fastening Tissue," the entire contents of which are expressly incorporated by reference herein.

FIELD OF THE INVENTION

The present invention relates to medical devices and methods. In particular, the present invention relates to a system, apparatus, and method for fastening tissue, and particularly for fastening tissue using a suture and clip.

BACKGROUND OF THE INVENTION

Many medical procedures involve joining tissue pieces. Suturing adjacent tissue pieces is commonly performed using suture, particularly where the tissue pieces are easily accessible to the surgeon. In conventional surgical techniques, the surgeon will secure the tissue pieces by forcing a needle and suture material through various portions of the tissue, and then tying a knot in the suture material to secure the tissue pieces.

Minimally invasive surgical techniques have emerged as an alternative to conventional surgical techniques to perform a plurality of surgical procedures. Minimally invasive procedures differ from conventional surgical procedures in that a plurality of devices may be introduced into the body through a small incision. As a result, trauma to the body is greatly reduced, thereby decreasing the recovery time of the patient.

Percutaneous and other minimally-invasive methods of surgery, where the surgery may be performed remotely via catheters, often include the need to fasten tissue pieces which the surgeon cannot directly access. For example, in percutaneous operations to close a patent foramen ovale (PFO), adjacent tissue pieces on either side of the PFO must be secured together via a catheter. Further description of such PFO procedures is included in co-pending patent application Ser. No. 11/174,143, filed concurrently herewith and entitled "System, Apparatus, and Method for Repairing Septal Defects," the entire contents of which are expressly incorporated herein by reference.

One challenge presented when performing a heretofore conventional surgical procedure using a minimally invasive technique is to remotely position and secure sutures to an area of interest. In minimally invasive surgical techniques the surgeon's access to the approximation site is greatly reduced. One method involves using a surgical device to attach the suture material to the tissue, while allowing for sufficient suture so that the suture ends lead outside of the patient's body for easy access by the surgeon. The surgeon can remotely form a loose knot in the suture material and advance the knot to the tissue within the patient using a so-called "knot pusher." The surgeon can then remotely tighten the suture and knot, thereby securing the tissue pieces together.

Several knot pushing devices are known which permit an operator to push suture knots which have been formed extracorporeally towards tissue to be sutured. For example, U.S. Pat. No. 5,769,863, issued to Garrison et al., discloses a surgical knot pusher having an elongated body connected to a pushing head. The pushing head engages a portion of suture material containing a knot and is advanced to the area of interest, thereby "throwing" the knot. Once the suture knot is placed the knot pushing device is removed and a cutting implement is introduced into the body and cuts the remaining suture material. The remaining suture material is then removed. Another example of a knot pusher is disclosed in U.S. Pat. No. 6,860,890, entitled "Surgical Knot Pushing Device and Method of Use," the entire contents of which are expressly incorporated herein by reference.

In light of the foregoing, there is presently a need for improved systems for remotely securing tissue pieces. More specifically, there is a present need for an improved method, apparatus, and system for fastening tissue. The current invention meets this need.

BRIEF SUMMARY OF THE INVENTION

The present invention solves the problem of effectively securing tissue pieces using a suture and clip. Additionally, the present invention provides a device capable of securing and cutting suture via a catheter from a remote insertion location.

The present invention utilizes two separate and distinct handle movements to deploy a fastener and cut the suture. In a first embodiment, a rotational handle movement is used to deploy the fastener and a longitudinal handle movement is used to cut the suture ends. In another embodiment, a longitudinal handle movement is used to deploy the fastener and a rotational handle movement is used to cut the suture ends.

An embodiment of the invention includes a suture cutting catheter where a rotational handle movement and a rotational inner body movement cuts suture ends. The suture cutting catheter may include an inner body comprising an angled distal face, and a main body comprising a distal opening and a cutting recess through which suture may pass.

In a method according to the invention, the user deploys suture through tissue within a patient's body, leaving one or more suture leads that pass out of the patient's body. A catheter according to the invention is advanced into the patient's body along the suture leads, positioned adjacent the tissue, and the catheter cuts the suture leads at a position near the tissue. The catheter may also be used to deploy a clip or other fastener to secure the suture in place in the tissue.

Other objects, features, and advantages of the present invention will become apparent from a consideration of the following detailed description.

BRIEF DESCRIPTION OF THE DRAWINGS

FIG. 7b depicts a cross-sectional view of the catheter of FIG. 7a, taken along the line 7b-7b depicted in FIG. 7a;

FIG. 7c depicts a front view of the stationary plate of FIG. 7a;

FIG. 7e depicts a perspective view of a portion of the internal structure of the catheter of FIG. 7a;

FIGS. 8a-8c depict side views, in partial cross-section, of the catheter proximal portion, including handle, of the catheter of FIG. 7a;

FIG. 9b depicts a bottom view, in partial cross-section, of the catheter proximal portion, including handle, of FIG. 9a;

FIG. 12b depicts a perspective view of a distal portion of the suture cutting catheter of FIG. 12a;

FIG. 12c depicts a side view, in cross-section, of a distal portion of the suture cutting catheter of FIGS. 12a and 12b;

FIG. 13b depicts a side view, in cross-section, of the distal opening structure of FIG. 13a;

FIG. 14b depicts a side view, in cross-section, of a distal end of the catheter with outer sheath of FIG. 14a; and FIG. 14c depicts a top view of the outer sheath of FIG. 14a.

DETAILED DESCRIPTION OF THE INVENTION

The invention is an apparatus, system, and method for securing suture. More specifically, the invention provides for percutaneous or other minimally-invasive techniques of securing and cutting of suture.

Figure 1:
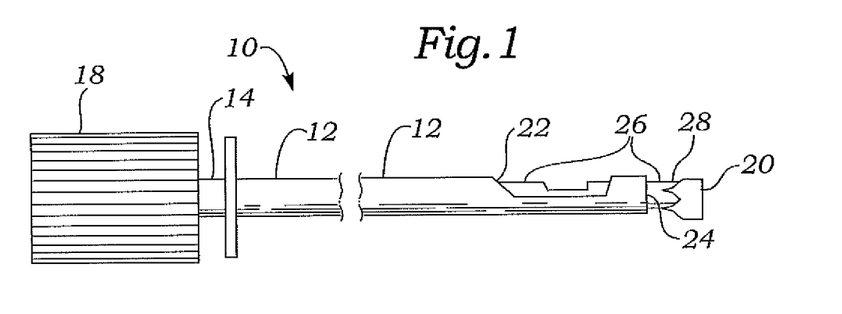
FIG. 1 depicts a side view of a catheter according to an embodiment of the invention.

FIG. 1 depicts an embodiment of a fastener catheter 10 according to an embodiment of the invention. The fastener catheter 10 has a generally tubular main body 12, a proximal end 14, and a distal end 16. The proximal end 14 includes a handle knob 18. The distal end 16 includes a suture clip 20 positioned thereon. The fastener catheter 10 may be manufactured in a variety of shapes, sizes, lengths, widths, and biologically-compatible materials as desired for a particular application.

The generally tubular main body 12 has a longitudinal inner lumen 22 therethrough which terminates in a distal opening 24. A longitudinally slidable inner body 26 is slidably positioned within the main body 12. The inner body 26 includes an inner tubular member distal end 28 which extends out of the main body distal opening 24. The inner tubular member distal end 28 itself includes an inner tubular member distal opening 30, which leads to an inner body lumen 32. These and other features are depicted in additional detail in FIGS. 2a-2c, which illustrate (in exploded fashion in FIGS. 2a-3b, and assembled in FIG. 2c), distal portions of the fastener catheter 10.

Figures 2A, 2B:
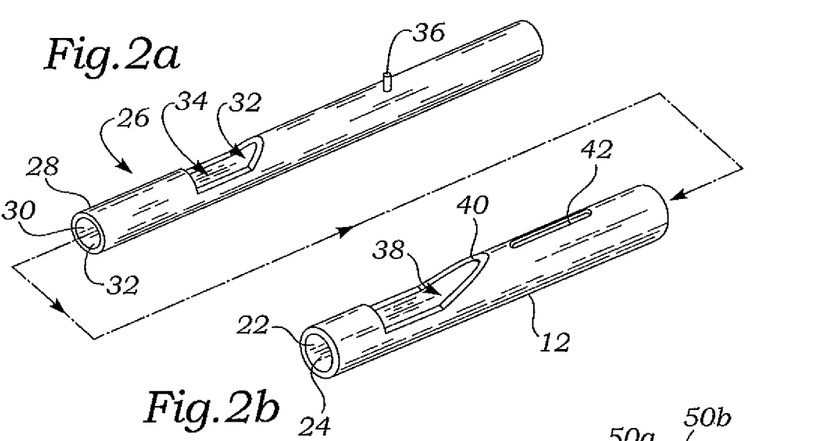
FIGS. 2a and 2b show a perspective view of components of the catheter distal portion of an embodiment of the present invention.

The inner body 26 includes a suture recess 34 formed in the side thereof, which in turn is in communication with the inner body lumen 32. Inner body 26 also includes a pin 36 extending radially outward therefrom. The main body 12 has a cutting recess 38 formed in an axial side thereof and a cutting member 40 which, in the embodiment depicted, is on a proximal edge of cutting recess 38. A pin recess in the form of slot 42 extends parallel to the axis of the main body 12 and radially through to main body lumen 22. The slot 42 is thus configured to receive pin 36 in sliding relation.

Figure 2C:
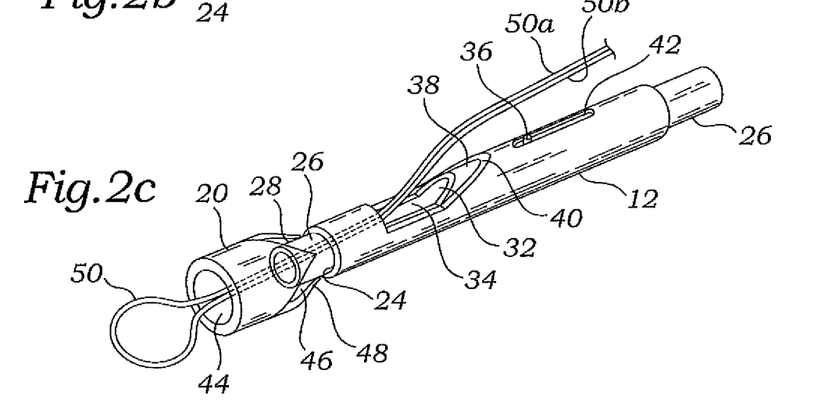
FIG. 2c shows a perspective view of the catheter distal portion the embodiment from FIGS. 2a and 2b assembled and having a fastener attached thereto.

In FIG. 2c, the inner body 26 is slidably positioned within main body 12, such that suture recess 34 is in alignment with cutting recess 38. Pin 36 is in slidable communication with slot 42 thereby permitting relative linear motion, but preventing relative rotational motion, between inner body 26 and main body 12. A clip 20 is positioned on the inner body distal end 28, which protrudes from the main body distal opening 24. The clip, which is depicted in greater detail in FIGS. 3a-3b, includes a clip distal opening 44, clip proximal opening 46, and engagement members 48. As depicted in FIG. 2c, the clip 20 has been placed on inner member distal end 28 by deflecting the engagement members 48 radially outward until they can be placed around the outer circumference of inner body distal end 28. Accordingly, the clip 20 is secured to the inner body distal end 28 by means of the frictional engagement between the engagement members 48 and the outer surface of inner body 26. Suture 50 extends from the fastener clip 20, with suture leads 50a and 50b extending through the clip distal opening 44, engagement members 48, and proximal opening 46, passing through inner member distal opening 30 and inner member lumen 32, exiting the inner member 26 via suture recess 34, and exiting the side of main body 12 through cutting recess 38.

Figure 3A:
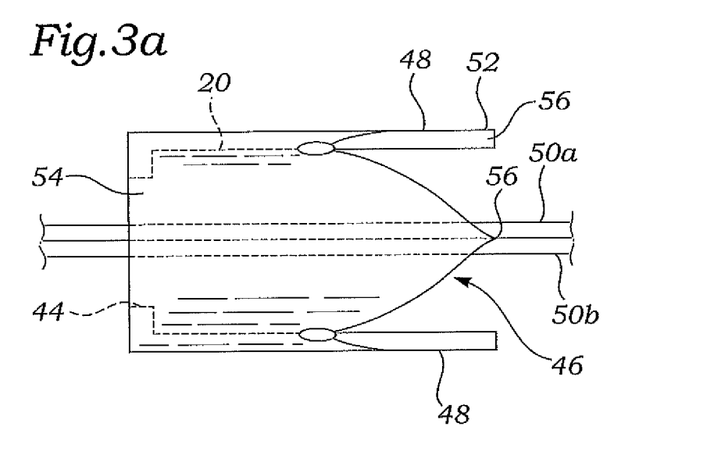
FIGS. 3a and 3b depict side views of a fastener according to an embodiment of the invention.
Figure 3B:
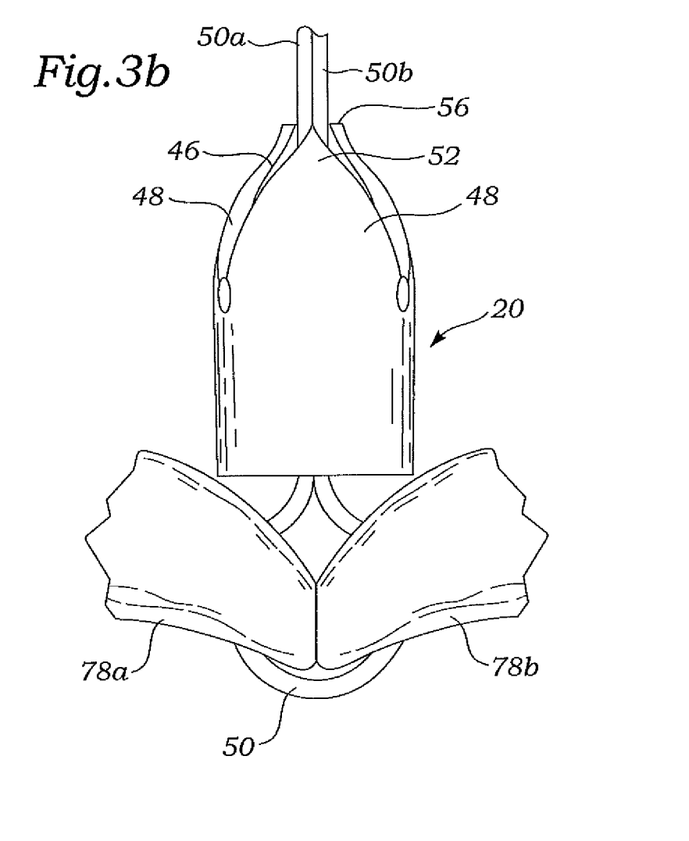

FIGS. 3a and 3b illustrate a fastener 20 of the present invention. Fastener 20 may be manufactured from a variety of materials including, for example, Nickel-Titanium alloys, shape-memory alloys, stainless steel, titanium, various plastics, and other biologically-compatible materials. Fastener 20 has a distal opening 44 leading to an internal attachment lumen 54 extending axially through the clip 20, including passing through the one or more engagement member(s) 48 formed on a proximal end 52 thereof. Between the engagement members 48 is defined proximal opening 46, which in the embodiment depicted acts as an engagement aperture. The proximal opening 46 is in communication with internal attachment lumen 54. Attachment lumen 54 and proximal opening 46 are sized to receive a first suture lead 50a and a second suture lead 50b therein. Prior to deployment, engagement member(s) 48 are deflected radially away from the axis of the fastener clip 20 such that proximal opening 46 has a relative large first diameter sufficient to permit suture leads 50a and 50b to slide therethrough, as depicted in FIG. 3a. Upon deployment, i.e. after the suture leads 50a and 50b have been retracted, engagement members 48 are deflected or permitted to spring back toward the central axis of the fastener 20 such that the proximal opening 46 assumes a second smaller diameter compressing and securing suture leads 50a and 50b in place, as depicted in FIG. 3b.

Depending on the particular embodiment, including the materials from which a particular fastener is made, the engagement member(s) 48 may tend to spring toward a natural position at the axis of fastener 20. FIG. 3b shows the fastener 20 in the deployed configuration in which suture leads 50a, 50b are secured in fastener 20. Each engagement member 48 may further include a pointed tip 56 which, when the engagement member(s) are in the deployed position, engages and further restricts movement of the suture leads 50a, 50b. Other fasteners may also be used without departing from the scope of the invention. Examples of some fasteners are set forth in co-pending U.S. patent application Ser. No. 10/389,721, filed May 14, 2003 and entitled "Mitral Valve Repair System and Method of Use," the contents of which are incorporated herein by reference in their entirety.

Figure 4A:
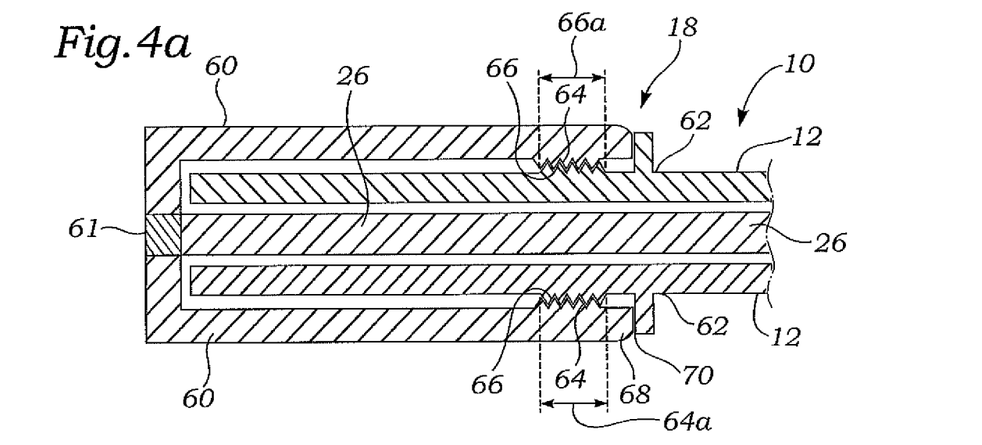
FIGS. 4a-4c depict side views, in partial cross-section, of a catheter proximal portion, including handle, according to an embodiment of the invention.
Figure 4B:
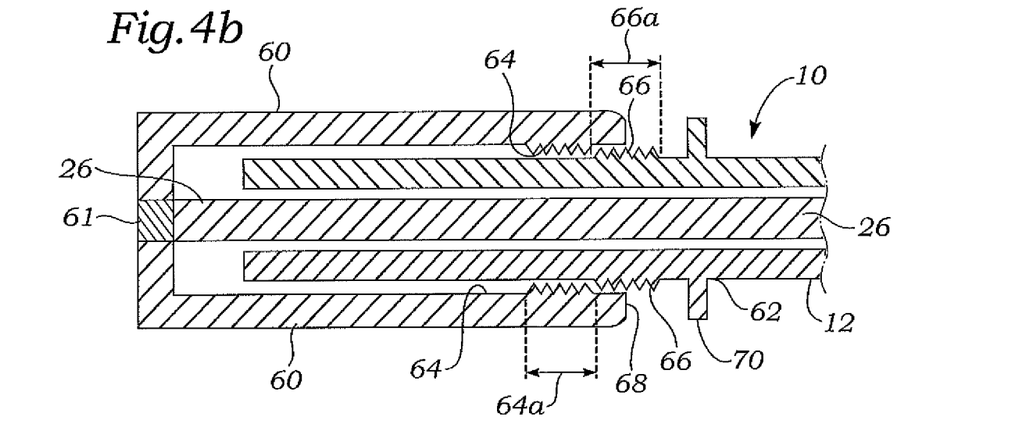
Figure 4C:
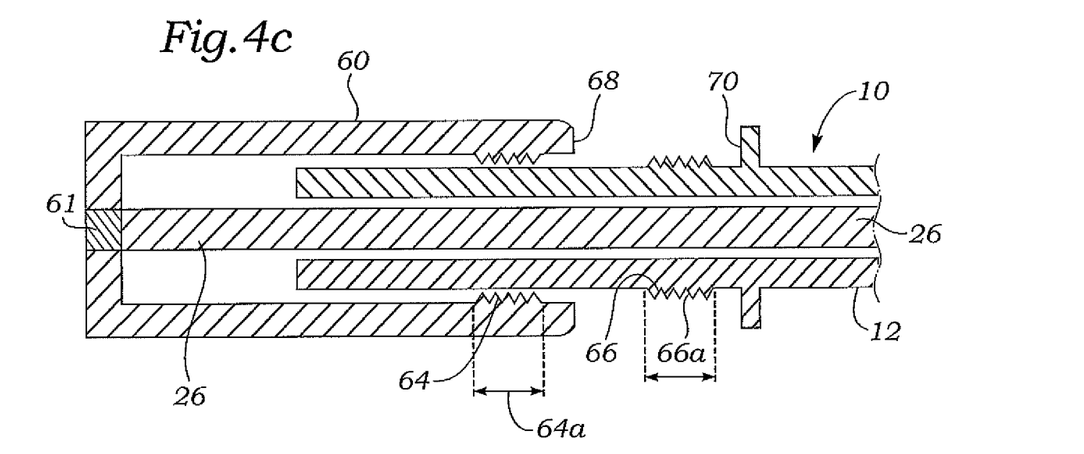

FIGS. 4a-4c depict the handle portion 18 of the catheter 10, which includes a rotatably and slidably movable portion 60 and a stationary portion 62. In the embodiment depicted, the movable portion 60 is rotatably and slidably positioned about the stationary portion 62. The movable portion 60 is secured to the catheter inner body 26 via a rotational hub 61 which permits rotational but not longitudinal movement of the movable portion 60 with respect to inner body 26. The stationary portion 62 is secured to the catheter main body 12. Accordingly, longitudinal movement of the movable portion 60 with respect to the stationary portion 62 causes corresponding longitudinal movement of the catheter inner body 26 with respect to the catheter main body 12. In the embodiment of FIGS. 4a-4c, the movable portion 60 includes an inward-facing threaded surface 64 configured to interact with an outward-facing threaded surface 66 on the stationary portion 62. Rotational movement of the movable handle portion 60 will cause the threaded surfaces to interact. Accordingly, rotational movement of the movable handle portion 60 with respect to the stationary handle portion 62 will cause corresponding longitudinal movement of the movable handle portion 60 with respect to the stationary handle portion 62. Because the movable handle portion 60 is secured to the catheter inner body 26, and the stationary portion 62 is secured to the catheter main body 12, longitudinal movement of the movable handle portion 60 causes longitudinal movement of the catheter inner body 26 with respect to the catheter main body 12.

In the embodiment of FIG. 4a, the movable handle portion 60 is positioned with a distally-facing portion, namely its distal end 68, abutting a proximal-facing structure 70 of the stationary handle portion. Accordingly, distal longitudinal movement of the movable handle portion 60 with respect to the stationary handle 62 from the positioned depicted in FIG. 4a is prevented. Because a clockwise movement (in the case of a right-handed screw engagement system) of the movable handle portion 60 causes distal longitudinal movement, the proximal-facing edge 70 prevents not only (initial) distal proximal movement but also clockwise rotational movement of the movable handle portion 60.

When a user rotates the movable portion 60 counterclockwise with respect to the stationary portion 62, the movable portion 60 is longitudinally displaced proximally with respect to the stationary portion. In the embodiment of FIGS. 4a-4c, the threaded surfaces 64, 66 have only limited lengths 64a, 66a (measured along in the longitudinal direction of the catheter). After a certain amount of rotational movement, the inward threaded surface 64 will have moved proximally of the outward facing threaded surface 66, as depicted in FIG. 4b. At this point the movable portion 60 is no longer restrained by the threaded portion from direct (i.e., longitudinal as opposed to spiral) proximal movement with respect to the stationary portion 62. Once the movable portion 60 is in the position depicted in FIG. 4b, the user can pull the movable portion 60 proximally with respect to the stationary portion 62 handle, thereby moving the movable portion 60 to a position such as that shown in FIG. 4c.

In the embodiment of FIGS. 4a-4c, the movable handle portion 60 is depicted connected via a rotational hub connector 61 to inner body 26. The connection may, depending on the particular application, be by another method, either direct or indirect. For example, wires may lead from the movable handle portion 60 to the inner body 26. Other structures are also within the scope of the invention.

Figure 5A:
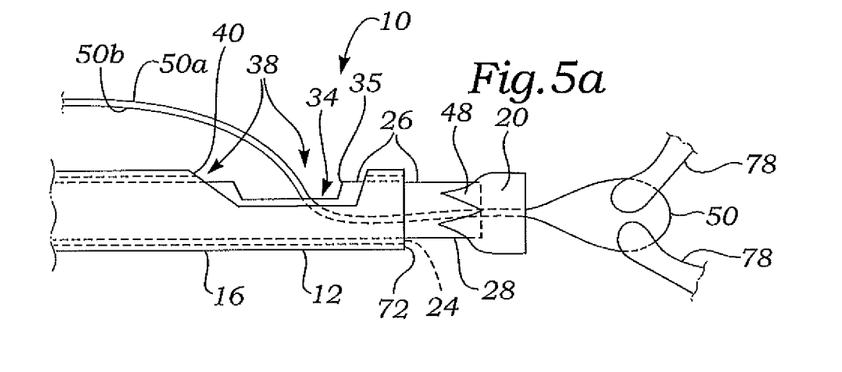
FIGS. 5a-5c depict side views of a catheter distal portion according to an embodiment of the invention.
Figure 5B:
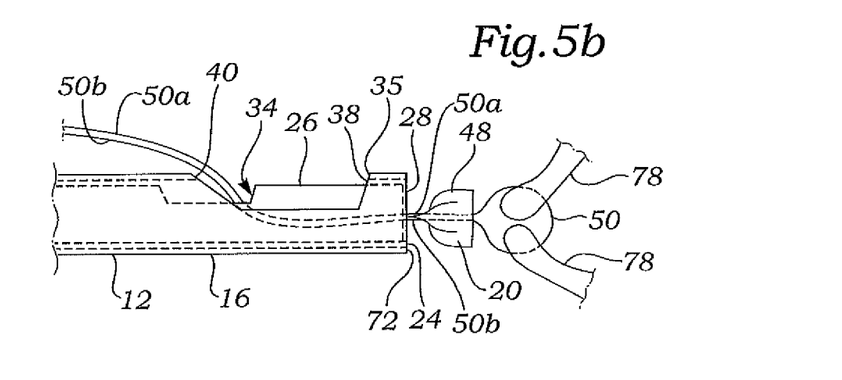
Figure 5C:
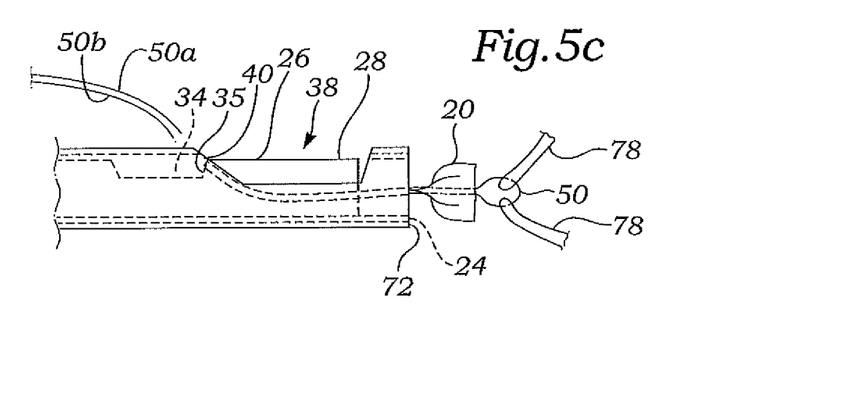

FIGS. 5a-5c depict the distal end 16 of the catheter 10, with the distal end configurations of FIGS. 5a-5c corresponding to the handle configurations of FIGS. 4a-4c, respectively. FIG. 5a depicts the catheter inner body distal end 28 extending from catheter main body distal opening 24, as would be the case with the movable portion 60 and stationary portion 62 positioned as depicted in FIG. 4a. FIG. 5a depicts a clip 20 positioned on the inner body distal end 28, with a suture line 50 extending into the assembly with suture leads 50a, 50b exiting the inner member 26 via suture recess 34, and exiting the side of main body 12 through cutting recess 38.

In FIG. 5b, the catheter inner body distal end 28 has been retracted into the main body distal opening 24, as would occur when the movable portion 60 and stationary portion 62 are positioned as depicted in FIG. 4b. With the inner body distal end 28 retracted, the clip 20 has been released from the catheter 10. As the inner body distal end 28 was retracted, the clip 20 engaged against the distal edge 72 of the main body distal opening 24 and was forced off of the inner body distal end 28. With the clip 20 freed from the catheter, the clip engagement members 48 have retracted axially, thereby partially or completely closing the clip proximal opening 46 and engaging the suture leads 50a, 50b. With the clip 20 in this closed configuration, the leads 50a, 50b are held fast and cannot move longitudinally within the clip 20. Note that the leads 50a, 50b still pass into the catheter 10, exiting the inner body 26 via suture recess 34 and exiting the side of main body 12 through cutting recess 38.

FIG. 5c depicts the inner body 26 retracted even further within main body 12, which corresponds to the configuration of movable portion 60 and stationary portion 62 depicted in FIG. 5c. As the inner body 26 was retracted, the suture leads 50a, 50b were caught in the engagement between the cutting member 40 of the main body 12 and a suture recess distal edge 35 of the inner body 26. The engagement of the cutting member 40 with the suture recess distal edge 35 cuts the suture leads 50a, 50b, allowing the user to remove the excess portions 74a, 74b thereof.

Although the embodiment depicted in FIGS. 5a-5c includes a cutting member 40 on the main body, a cutting member could be placed elsewhere, either in addition to or in lieu of the main body cutting member. For example, a cutting member could be placed on the suture recess distal edge 35 of the inner body 26. Or both the suture recess distal edge 35 and the main body cutting member may be unsharpened edges, with the suture being cut by the sheering force created by the cooperation between the relatively unsharp edges.

Figure 6:
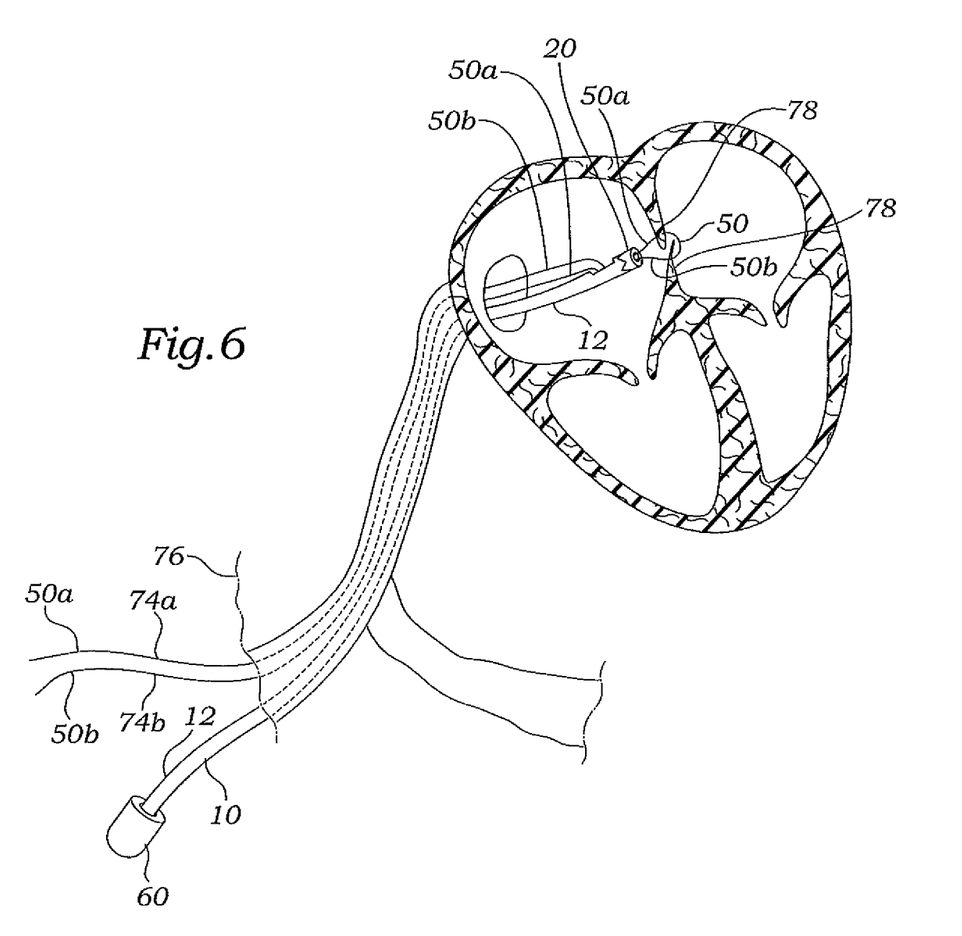
FIG. 6 illustrates a catheter advanced within a patient's vasculature and adjacent tissue pieces to be joined according to an embodiment of the invention.

FIG. 6 depicts the fastener catheter 10 deploying a fastener 20 at a desired location in a patient's body 76. In the embodiment depicted, the suture 50 has previously been passed through the desired tissue structure within the patient's body 76, which in the embodiment depicted is heart tissue 78. Various methods and/or systems can be used to pass the suture through the desired tissue. Examples of such a suturing methods and apparatuses are depicted and described in issued U.S. Pat. No. 6,626,930, issued to Allen et al.; co-pending U.S. patent application Ser. No. 10/106,583, entitled "Sequential Heart Valve Repair Device and Method of Use" and filed on Mar. 26, 2002; co-pending U.S. application Ser. No. 10/233,879, entitled "Single Catheter Mitral Valve Repair Device and Method for Use" and filed on Sep. 3, 2002; co-pending U.S. application Ser. No. 10/389,721, entitled "Mitral Valve Repair System and Method for Use" and filed on Mar. 14, 2003; and in co-pending U.S. patent application Ser. No. 11/174,143, filed concurrently herewith and entitled "System, Apparatus, and Method for Repairing Septal Defects"; the contents of each of which are expressly incorporated herein by reference. With the suture 50 passing through the tissue 78 and the suture leads 50a, 50b passing out of the patients' body 76, the user can advance the fastener catheter 10 into the vicinity of the tissue 78, as shown in FIG. 6. The fastener catheter will advance along the suture leads 50a, 50b and, if present, along the guidewire (not shown).

The user can initially tighten the suture 50 to determining whether the suture 50 is properly positioned in accordance with the desires of the user in the particular application. The advancement of the fastener catheter 10, combined with the user holding (and possibly pulling on) the suture leads 50a, 50b, causes the suture 50 to tighten. The user can verify the effectiveness of the tightened suture by monitoring various patient functions. For example, the user may confirm the result by monitoring blood flow using radiopaque dyes combined with fluoroscopy. If the user is dissatisfied with the results when the suture is initially tightened, the user can remove the suture entirely from the patient's body and repeat the suture deployment to try to achieve a better positioning of suture. If, however, the user is satisfied with the results, the user can release the clip 20 from the catheter 10, which in the handle embodiment of FIGS. 4a-4c is achieved by rotating the handle movable portion 60. Once the clip 20 is released, the clip securely holds the suture leads 50a, 50b. The user can then distally retract the handle movable portion 60 relative to the stationary portion, thereby cutting the suture leads 50a, 50b. The user can then remove the excess suture 74a, 74b by simply pulling the excess suture 74a, 74b out of the patient's body 76. The user then withdraws the fastener catheter 10 from the patient, leaving the suture 50 and suture clip 20 in place in the desired tissue. The guidewire, if present, is also removed.

FIGS. 7a-7e depict another embodiment of a catheter handle 10 according to the invention. The catheter includes a stationary handle portion 62 having proximal portion 80 and a distal portion 82. The stationary handle proximal and distal portions 80, 82 are rigidly connected to each other via one or more longitudinal elements 84. In the embodiment of FIGS. 7a-7e, there are two such longitudinal elements 84. The movable handle portion 60 has a threaded inner surface 86. A butterfly wheel 88 is positioned within the movable handle portion 60. The butterfly wheel 88 is connected to the inner body 26 via a spindle 93 and wire 89, so that proximal movement of the butterfly wheel 88 causes corresponding proximal movement of the inner body 26. The butterfly wheel 88 has a threaded outer surface 90 configured to engage the threaded inner surface 86 of the movable handle portion 60. The butterfly wheel 88 is held in alignment with the central axis 100 of the catheter via an axis rod 91 which passes proximally through the center of the butterfly wheel 88, and a distal spindle 93. The butterfly gear and distal spindle include a lumen 95 configured to slidingly receive the axis rid 91. In the embodiment depicted, the wire 89 at a proximal end is bonded to the spindle 93, and at a distal end is bonded to the inner body 26.

In the embodiment of FIGS. 7a-7e, there is a stationary plate 92 held rigidly with respect to the stationary handle portion 62, which can be accomplished by securing the stationary plate 92 to the handle portion longitudinal elements 84. The stationary plate has a hole 94 at a particular location thereon. The movable handle portion 60 is secured to a proximally-facing pinion alignment rod 96, which is at an identical radial distance 98 (depicted in FIG. 7a) from the movable handle portion rotational axis 100 as the radial distance 102 (depicted in FIGS. 7c-7d) of the hole 94. The alignment rod 96 is also sized to pass through the hole 94 when in alignment therewith. The stationary plate 92 also serves as the distal anchor for the spindle 93 and butterfly wheel 88.

Figure 7A:
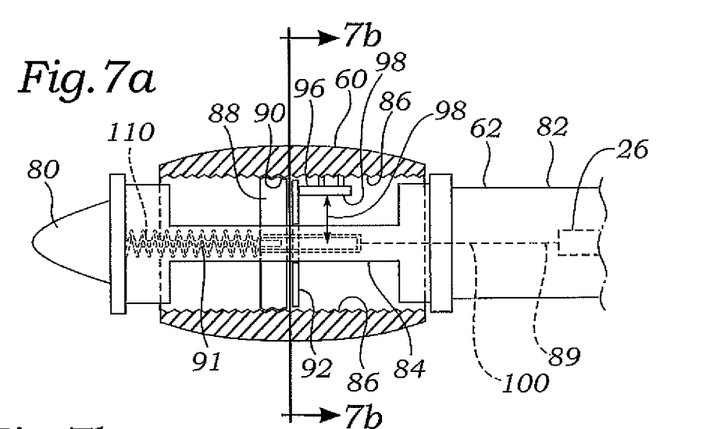
FIG. 7a depicts a side view, in partial cross-section, of a catheter proximal portion, including handle, according to an embodiment of the invention.
Figure 7B:
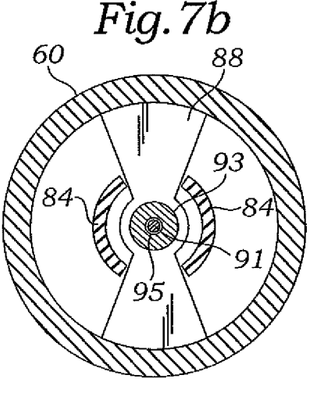
Figure 7C:
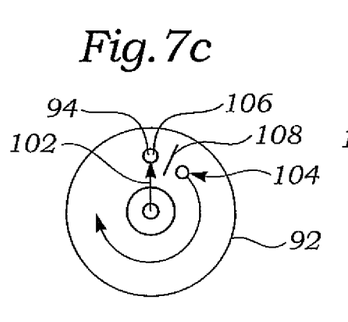
Figure 7D:
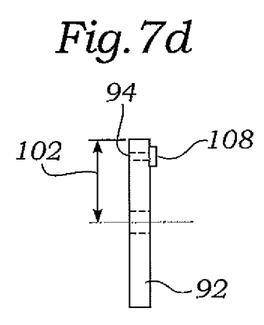
FIG. 7d depicts a side view of the stationary plate of FIGS. 7a and 7c.
Figure 7E:
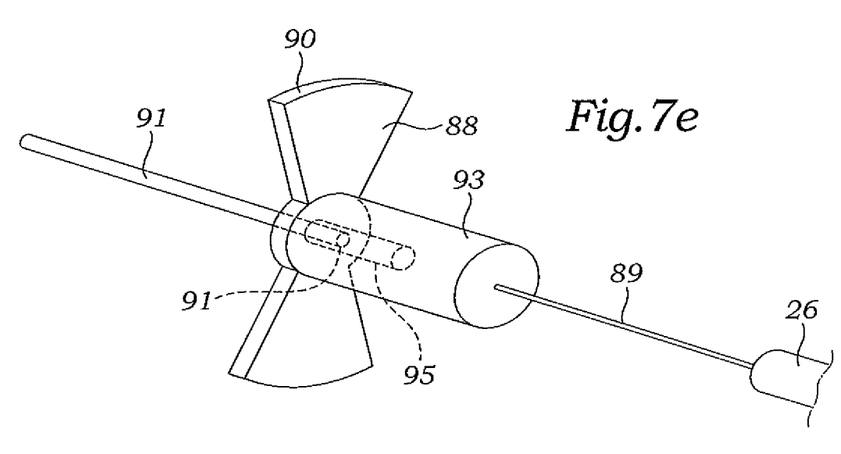

With the alignment rod 96 at a starting position 104, indicated in FIG. 7c, the rod 96 engages the stationary plate 92, thereby preventing proximal movement of the movable handle portion 60. The movable handle portion 60 is, however, able to be rotated. As the movable handle portion 60 is rotated, the threaded inner surface 86 of the movable handle portion 60 engages the threaded outer surface 90 of the butterfly wheel 88. The butterfly wheel 88 cannot rotate because it is held in rotational position by the stationary portion longitudinal elements 84. Instead of rotating, the butterfly wheel 88 is proximally displaced by the rotation of the movable handle portion 60. The proximal movement of the butterfly wheel 88 causes a corresponding proximal movement of the inner body distal end 28, so that the inner body distal end 28 retracts into the main body 12 and the clip is deployed, as was depicted in FIG. 4b.

At the same time that the butterfly wheel 88 is displaced proximally, the rotation of the movable handle portion 60 moves the pinion engagement rod from its starting (retrained) position 104 (depicted with respect to the stationary plate in FIG. 7c) to an alignment position 106, wherein the engagement rod 96 is in alignment with hole 94. With the rod 96 in alignment with the hole 94, the movable handle portion 60 is freed to move be moved proximally with respect to the stationary handle portion 62. The user can thus pull back on the movable handle portion 60 and move the main body cutting member 40 to cut the suture 50, as was depicted in FIG. 4c. In the embodiment of FIGS. 7a-7e, the stationary plate has an arresting member 108 that can engage the alignment rod 96 to prevent the movable member 60 from being rotated "backwards" from the starting point, and which can also prevent the movable member from being "over-rotated" such that the alignment rod goes past the hole 94. A spring 110 is also provided, which urges the butterfly wheel 88 and movable handle member 60 to a distal direction. The spring 110 thus serves to prevent the movable handle member 60 from being inadvertently moved in the proximal direction, even after the pinion engagement rod 96 is aligned with the hole 94. The spring 110 provides sufficient forward pressure to prevent inadvertent proximal movement of the movable handle member 60, but insufficient pressure to prevent the user from intentionally moving the movable handle member 60 proximally. When a user pulls the movable handle portion 60 proximally with a force greater than the spring force, the movable handle portion 60 moves proximally, thereby moving the inner body 26 proximally and severing the suture lines.

Figure 8A:
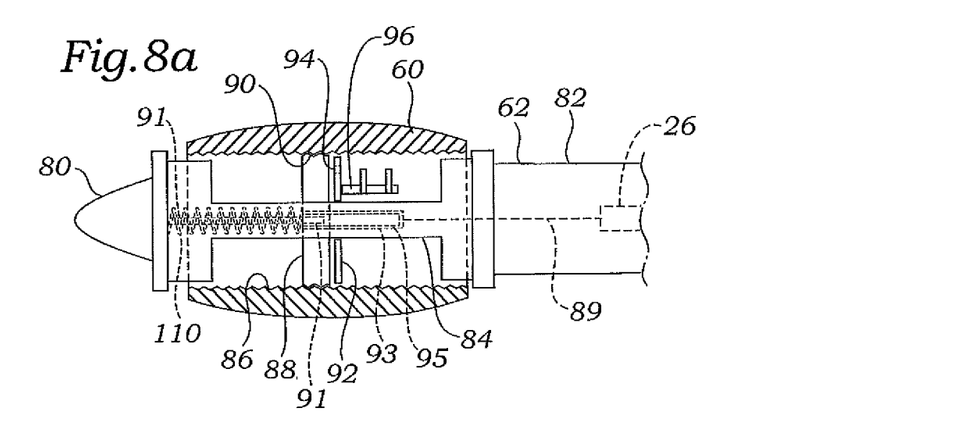
Figure 8B:
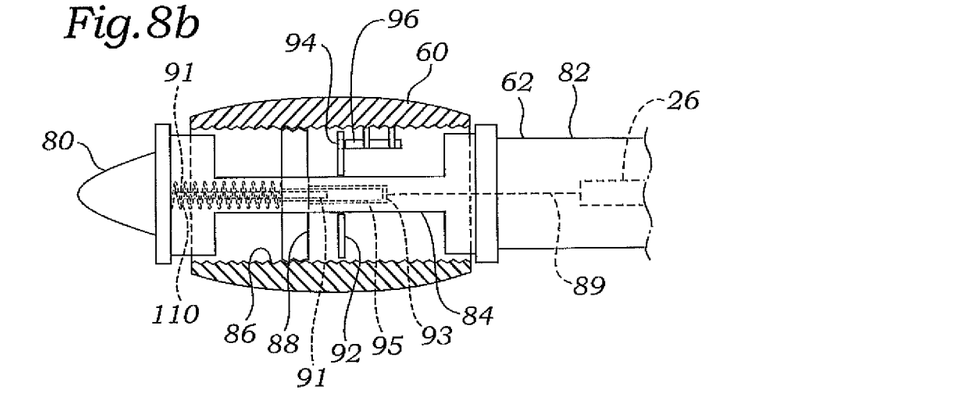
Figure 8C:
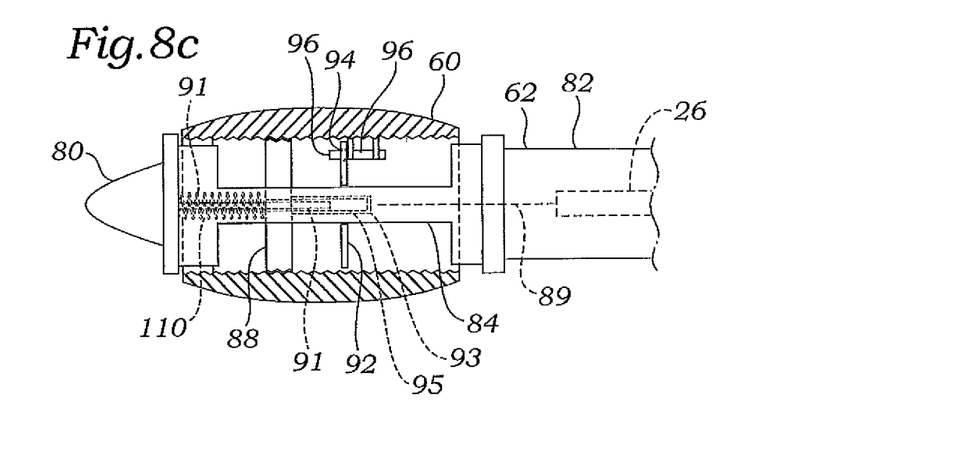

FIGS. 8a-8c depict the embodiment of FIGS. 7a-7e, with FIG. 8a depicting the handle in the "start" position (corresponding to the pre-clip-deployment configuration of the distal portion depicted in FIG. 4a). As the movable handle portion 60 is rotated, the butterfly gear 88 is moved proximally. Because the butterfly gear 88 is connected via the spindle 95 and wire 89 to the inner body 26, the proximal movement of the butterfly gear 88 causes corresponding proximal movement of the inner body 26. Note that the connection between the inner body and butterfly gear may be direct or indirect, depending on the particular application.

FIG. 8b depicts the movable handle portion 60 rotated to the point where the pinion alignment rod 96 is in alignment with the hole 94. At this point the butterfly gear 88 has moved proximally an amount sufficient to withdraw the inner body distal end 28 within the main body 12 to release the clip 20, as depicted in FIG. 4b.

With the pinion alignment rod 96 in alignment with the hole 94, the movable handle portion 60 can be moved proximally with respect to the stationary handle portion 62. By pulling the movable handle portion 60 proximally against the resisting force of the spring 110, the user moves the movable handle portion 60 and the butterfly gear 88 proximally as depicted in FIG. 8c. Moving the movable handle portion 60 and butterfly gear 88 to the position depicted in FIG. 8c causes corresponding proximal displacement of the inner body distal end 28 with respect to the main body 12, thereby moving the main body cutting member 40 to cut the suture 50, as was depicted in FIG. 4c.

Figure 9A:
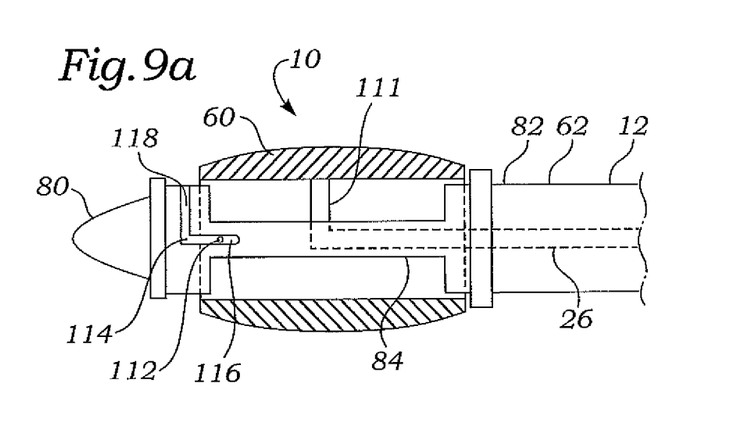
FIG. 9a depicts a side view, in partial cross-section, of a catheter proximal portion, including handle, according to an embodiment of the invention.
Figure 9B:
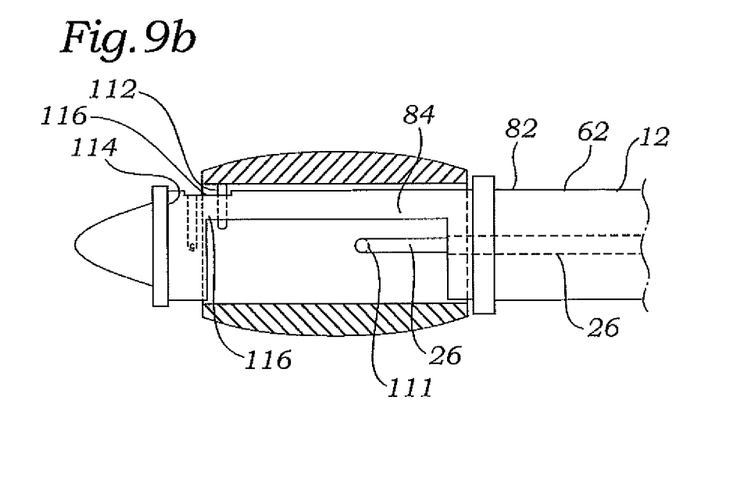
Figure 9C:
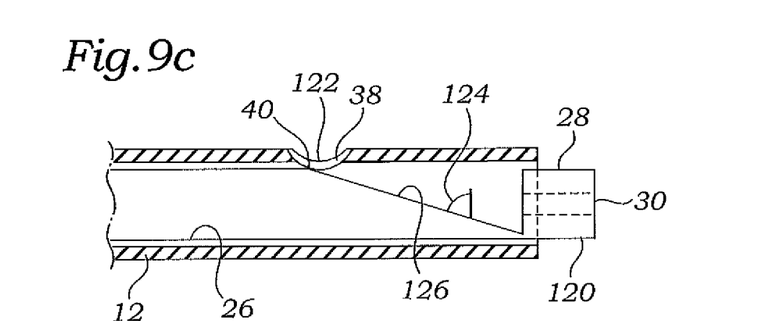
FIG. 9c depicts a side view, in partial cross-section, of a catheter distal portion of the catheter of FIGS. 9a and 9b.

In another embodiment of the invention, proximal displacement of the movable handle portion causes clip deployment, while rotational movement of the movable handle portion causes cutting of the suture. FIGS. 9a-9c depict an example of such a catheter 10. The proximal end is depicted in FIGS. 9a and 9b. Movable handle portion 60 is secured to the inner body 26, which in the embodiment depicted is accomplished via an L-shaped connection 111, with the stationary handle portion 62 secured to the main body 12. The movable handle portion 60 is configured to rotate and to move longitudinally with respect to the stationary handle portion 62. An inward-facing post 112 on the movable handle portion 60 cooperates with a groove or slot 114 on the stationary handle portion 60. The slot 114 includes a longitudinal portion 116 and a circumferential portion 118, with the circumferential portion 118 passing at least partially about the circumference of the stationary handle portion 60. When the movable handle portion 60 is positioned with the post 112 in the longitudinal portion 116 of the slot 114, rotational movement of the movable handle portion 60 is prevented.

In the embodiment of FIG. 9c, the inner body distal end 28 includes a clip-receiving portion 120 configured to receive a clip thereon. The clip-receiving portion 120 includes an inner body distal opening 30 configured to receive suture therethrough. Just proximal of the clip-receiving portion 120 is a generally solid beveled surface 122. The beveled surface 122 is at an angle 124, which in the embodiment depicted is about 45 degrees. Other angles are also within the scope of the invention, depending on the particular application. The beveled surface may be generally flat, or may form an arc or other shape. The beveled surface includes an edge portion 126 which may be relatively sharp. The main body 12 includes a recess 38 in the side thereof. The recess 38 includes a cutting member 40 in a side edge thereof. Rotation of the inner body 26 causes the inner body beveled edge portion 126 to move adjacent to and cooperate with the main body cutting member 40 to cut any suture caught therebetween.

Figure 10A:
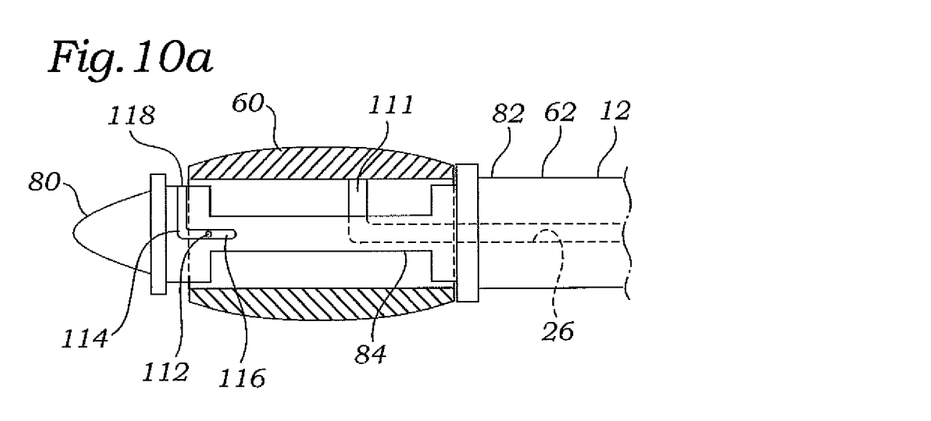
FIGS. 10a-10c depict side views, in partial cross-section, of various configurations of the catheter proximal portion, including handle, of FIGS. 9a-9b.
Figure 10B:
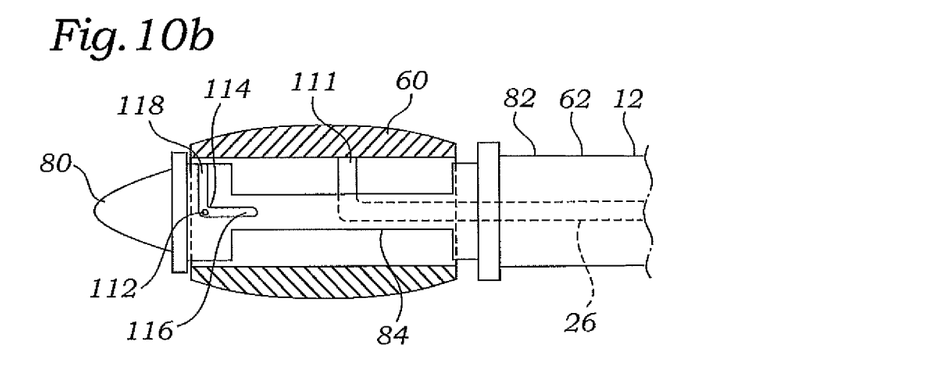
Figure 10C:
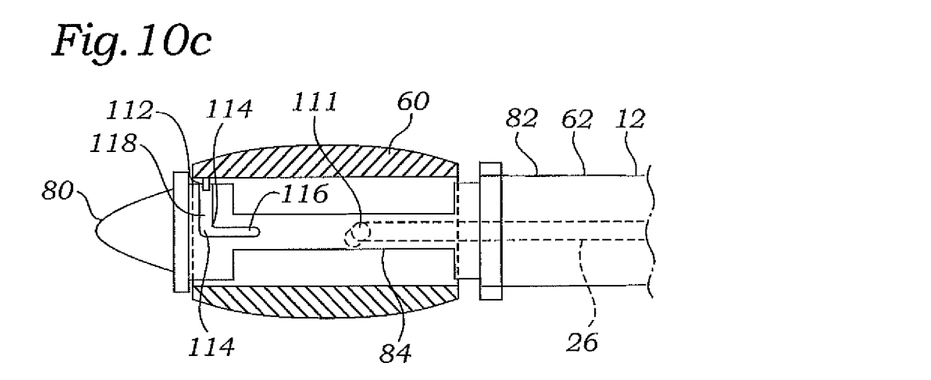
Figure 11A:
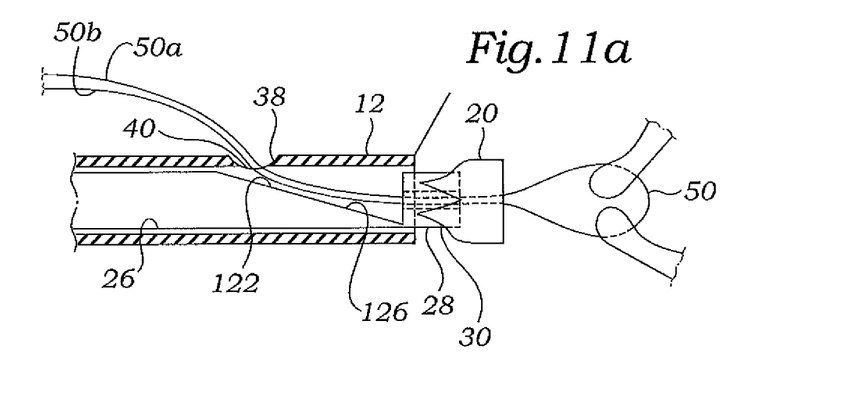
FIGS. 11a-11c depict side views, in partial cross-section, of various configurations of the catheter distal portion, including fastener, of FIG. 9c.
Figure 11B:
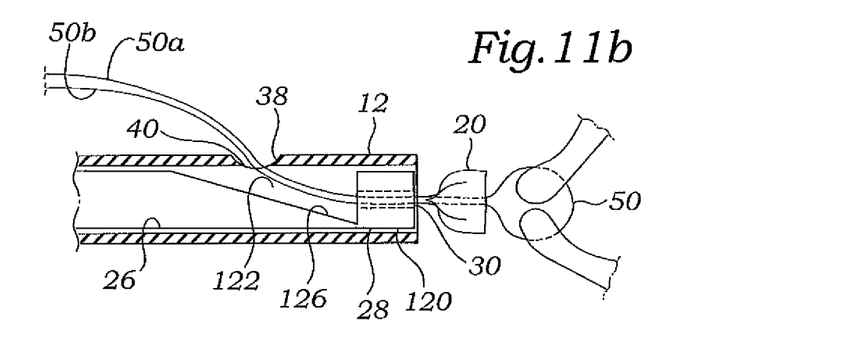
Figure 11C:
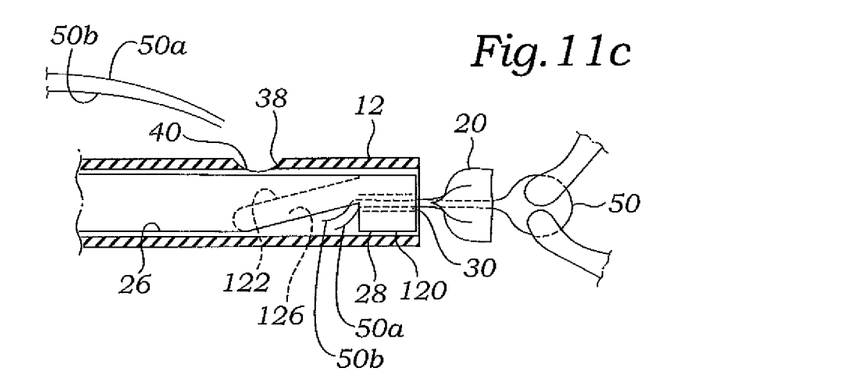

FIGS. 10a-10c depict positioning of the movable and stationary handle portions 60, 62, with FIGS. 11a-11c depicting corresponding positioning of the catheter inner body distal end 28 and main body 12. In FIG. 10a, the movable handle portion 60 is in the "start" position, which in the embodiment depicted has the movable handle portion 60 at a distal position with respect to the stationary handle portion 62. With the movable handle portion 60 in this position, the post 112 lies within the longitudinal portion 116 of the slot 114, thereby preventing rotational movement of the movable handle portion 60. The movable handle portion 60 can still be moved longitudinally, particularly in the proximal direction. With the movable handle portion 60 in the "start" position of FIG. 10a, the inner body distal end 28 protrudes from the main body 12, as depicted in FIG. 11a. A clip 20 is positioned on the protruding inner body distal end 28, with suture leads 50a, 50b passing within the clip 20, into the catheter 10, and out the main body cutting recess 38.

Proximal movement of the movable handle portion 60 with respect to the stationary handle portion 62 causes the inner body distal end 28 to retract within the main body 12. FIG. 10b depicts the movable handle portion 60 retracted proximally with respect to the stationary handle portion, with FIG. 11b depicting the corresponding position of the inner body distal end 28, which is retracted within the main body 12. The retraction of the inner body distal end 28 causes the clip 20 to be released, with the released clip 20 securing the suture 50. The new position of the movable handle portion 60 places the post 112 within the circumferential portion 118 of the slot 114, thereby permitting rotational movement of the movable handle portion 60.

Once the movable handle portion 60 has been retracted to the position of FIG. 10a, thereby releasing the clip 20 and securing the suture 50, the user can cut the suture leads 50a, 50b by rotating the movable handle portion 60. This rotation of the movable handle portion 60 causes the main body cutting element 40 to move adjacent to and cooperate with the inner body cutting edge 126, with the suture leads 50a, 50b caught between and severed by the scissor-like action between the main body cutting member 40 and the inner body cutting edge 126. With clip 20 deployed and the suture leads 50a, 50b severed, the user can withdraw the catheter 10 from the patient's body.

Although the embodiment depicted in FIGS. 9a-9c includes two sharpened elements, namely the main body cutting member 40 and the inner body cutting edge 126, providing only one such sharpened edge, or no sharpened edge at all, is within the scope of the invention. Moreover, the edges could be located on different parts of the apparatus. For example, the main body cutting member 40 may be replaced with an unsharpened edge, so that the actual cutting is performed by the inner body cutting edge 126. Alternatively, the inner body cutting edge 126 may be replaced with an unsharpened edge, so that the actual cutting is performed by the main body cutting member 40. Or both the inner body cutting edge 126 and the main body cutting member 40 may be replaced by unsharpened edges, with the suture being cut by the sheering force created by the cooperation between the relatively unsharp edges.

Figure 12A:
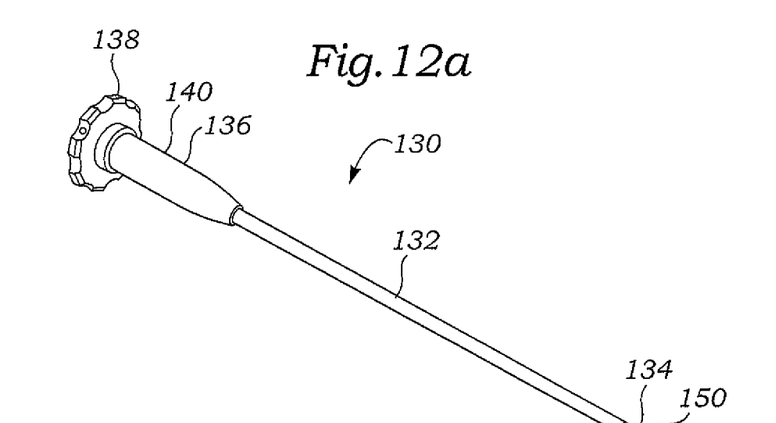
FIG. 12a depicts a perspective view of a suture cutting catheter according to an embodiment of the invention.
Figure 12B:
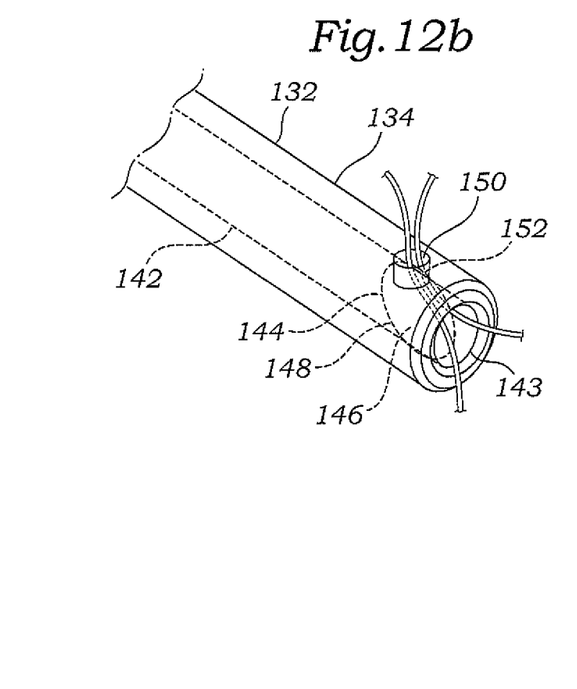
Figures 12C, 13B:
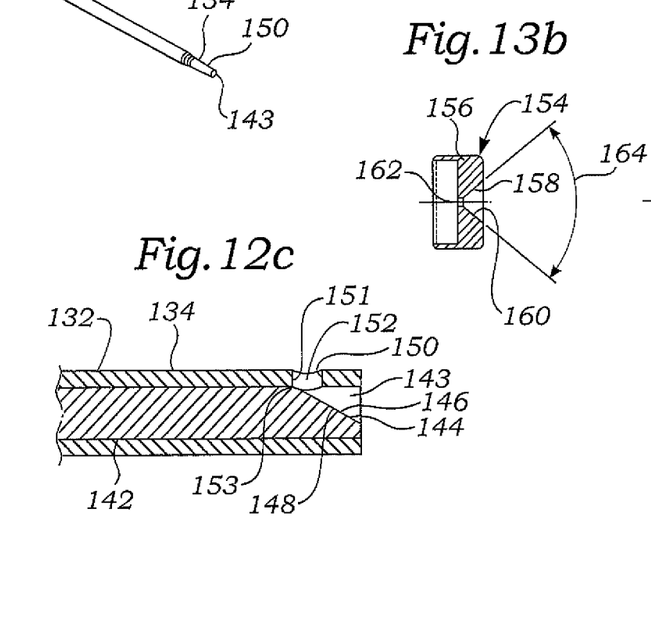

The cutting devices and methods described herein may be used with the clip deployment structure, as discussed above, or as a separate catheter and method for suture cutting without clip deployment. For example, FIGS. 12a-12c depict a catheter 132 configured for suture cutting, which can be used in percutaneous or other minimally-invasive procedures where it is desirable to remotely cut suture lines. The suture cutting catheter 132 could be used as discussed above with respect to cutting suture that has been secured with a clip, and could also be used to cut suture that has already been remotely tied, such as where a knot pusher has been used to advance a knot along suture to a desired site in a patient's body.

In the embodiment of FIG. 12a-12c, a suture cutting catheter 130 has a main body 132, a distal portion 134, and a proximal portion 136. The proximal portion 136 includes a rotatable handle portion 138 and a stationary handle portion 140. The catheter 130 has an inner body 142 rotatably received within the main body 132. The rotatable handle portion 138 is connected, directly or indirectly, to the inner body 142, so that rotation of the rotatable handle portion 138 causes corresponding rotation of the inner body 142. The stationary handle portion 140 is connected, directly or indirectly, to the main body 142.

FIGS. 12b and 12c depict the distal portion 134 in greater detail. The main body 132 has a distal end opening 143. Inner body 142 has a distal end 144 defining a beveled surface 146. The beveled surface includes a sharpened edge portion 148. The main body 132 includes a recess 150 in the side thereof. The recess 150 includes a cutting member 152 in a side edge thereof. Rotation of the inner body 142 with respect to the main body 132 causes the inner body sharpened edge portion 148 to move adjacent to and cooperate with the main body cutting member 152 to cut any suture caught therebetween.

Suture lines 50a, 50b (depicted in FIG. 12b) pass through the distal opening 143 and out of the recess 150. In order to facilitate the threading of the suture lines 50a, 50b, the inner body 142 can be positioned longitudinally within the main body 132 such that a proximal edge 153 of the beveled surface 146 is in alignment with a proximal edge 151 of the recess 150, as depicted in FIG. 12c. Such alignment provides a generally smooth path along which the suture leads 50a, 50b can be threaded, with the beveled surface 146 effectively forming a ramp leading to the recess 150. Positioning the beveled surface proximal edge 153 just distal of the recess proximal edge 151 will also provide a generally smooth and convenient path through which the suture leads 50a, 50b may be inserted.

Figure 13A:
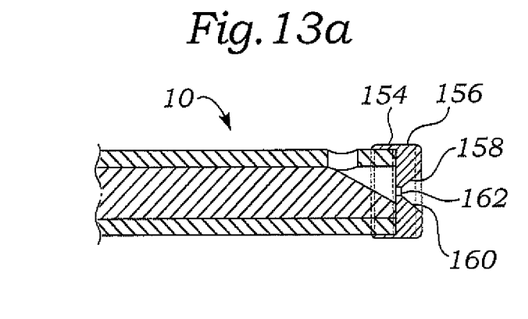
FIG. 13a depicts a side view, in cross-section, of a distal portion of a catheter, including distal opening structure, according to an embodiment of the invention.
Figure 13C:
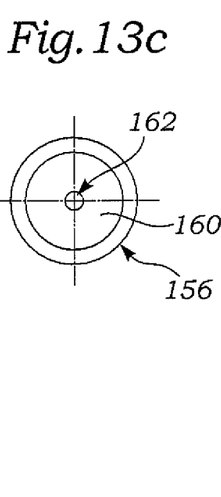
FIG. 13c depicts a front view of the distal opening structure of FIGS. 13a and 13b.

FIGS. 13a-13c depict a catheter 10 according to the invention provided with a distal opening structure 154 configured to facilitate the introduction of suture therein. In the embodiment of FIGS. 13a-13c, the distal opening structure 154 is a distal cap 156 which is secured to the distal end of the catheter main body 12. The distal cap 156 includes a distal opening 158, with the distal opening 158 including a generally funnel-shaped entrance 160 to help guide suture into an entry lumen 162. In the embodiment depicted, the funnel-shaped entrance defines an angle 164 of about 100 degrees. The distal cap may be formed as an integral part of the main body, or may be a separate structure secured to the main body 12 by glue (such as Loctite) or some other method, as in the distal cap 156 depicted in FIGS. 13a-13c. For a catheter configured to deliver a clip, a distal opening structure such as that depicted in FIGS. 13a-13b could be located on the distal portion of the clip itself, either in addition to or in lieu of a distal opening structure on the catheter itself. Note that the distal opening structure 154 is compatible with all catheter embodiments of the invention, including the dedicated suture cutter of FIGS. 12a-12c and the combined clip delivery and suture cutting catheter depicted in FIG. 1 and elsewhere.

Figure 14A:
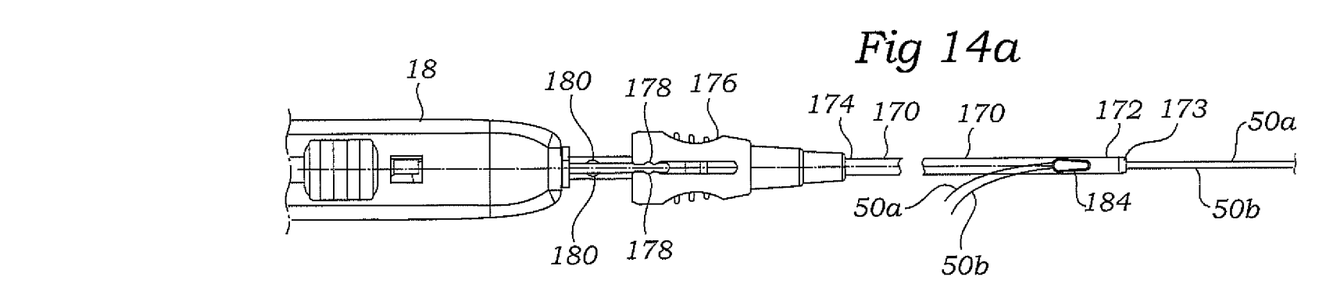
FIG. 14a depicts a top view of a catheter with outer sheath according to an embodiment of the invention.
Figure 14B:
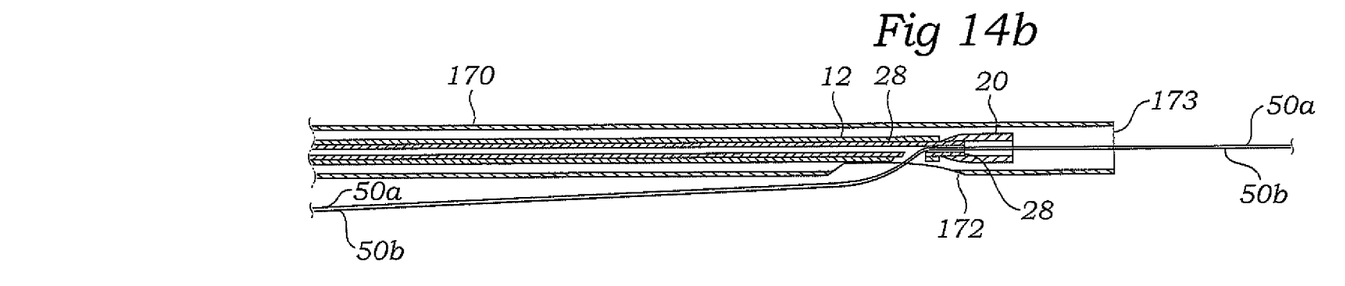
Figure 14C:
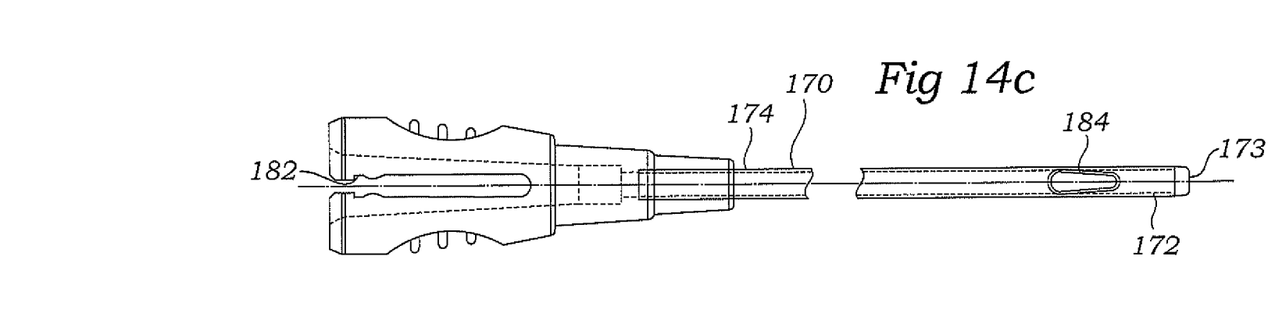

FIGS. 14a-14c depict a further embodiment of the invention. FIG. 14a depicts a top view of the catheter 10 with a protective outer sheath positioned 170 thereon, with FIG. 14b depicting a side view of the distal portion of the assembly of FIG. 14a. The catheter 10 includes a protective outer sheath 170 (depicted by itself in FIG. 14c) configured to be placed about and longitudinally moved along the catheter main body 12. The protective outer sheath 170 has a distal end 172 and a proximal end 174, with the distal end 172 having a distal opening 173. The proximal end 174 is connected to movable sheath handle 176. In the particular embodiment depicted, the movable sheath handle 176 is positioned distally of the main catheter handle 18. The apparatus includes a first arresting mechanism 178 and a second arresting mechanism 180 which cooperate an engagement mechanism 182 (depicted as indentations in FIG. 14c) on the movable sheath handle 176 to prevent inadvertent movement of the movable sheath handle 176. With the outer sheath 170 in a delivery position (depicted in FIGS. 14a and 14b), the distal end 172 of the protective outer sheath 170 extends over the main body 12 as well as the protruding inner body distal end 28 and the clip 20. The sheath 170 thus protects the clip 20, preventing the clip 20 from being inadvertently dislodged from the catheter 10 during advancement and positioning of the catheter distal end 16 within the patient's body. The sheath 170 includes a sheath cutout 184 which permits suture leads to pass from the main body cutting recess and out of the sheath 170.

Once the clip 20 is positioned at or near the desired deployment location within the patient's body, the user can proximally withdraw the movable sheath handle 176 with respect to the main catheter handle 18, thereby proximally withdrawing the outer sheath 170 to expose the clip 20 and inner body distal end 28. With the outer sheath 170 withdrawn, the clip 20 can be deployed and the suture 50 cut, as discussed previously.

While the invention has been described with reference to particular embodiments, it will be understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. Therefore, it is intended that the invention not be limited to the particular embodiments disclosed herein, but that the invention will include all embodiments falling within the scope of the appended claims.

What is claimed is:

1. An apparatus for fastening tissue, comprising:
an elongated body having a distal end and a proximal end, wherein the distal end terminates in a distal tip;
a clip releasably secured to and on the distal end of the elongated body, the clip comprising an inner lumen in which the distal tip of the elongated body is slidingly positioned;
a suture cutter at the elongated body distal end, the suture cutter configured to perform a cutting motion when activated;
a control element configured to be moved in a first direction and in a second direction, wherein the first direction is different from the second direction, and wherein the control element is configured to cause the elongated body distal tip to slidingly retract from the clip inner lumen when the control element is moved in the first direction, and the control element is further configured to activate the suture cutter when the control element is moved in the second direction, wherein the control element is configured to prevent movement of the control element in the second direction until after the control element has first been moved in the first direction, wherein the first direction is rotational about a longitudinal axis of the elongated body.

2. The apparatus of claim 1, wherein the second direction is longitudinal with respect to the longitudinal axis of the elongated body.

3. The apparatus of claim 1, wherein the control element is positioned at the proximal end of the elongate body.

4. The apparatus of claim 1, wherein the suture cutter comprises a first cutting element and a second cutting element.

5. The apparatus of claim 1, wherein the clip comprises at least one engagement member configured to frictionally engage the distal end of the elongated body when the clip is positioned thereon.

\* \* \* \* \*